(12) United States Patent
Menegaz et al.

(10) Patent No.: US 9,795,354 B2
(45) Date of Patent: Oct. 24, 2017

(54) METHOD AND APPARATUS FOR INCREASING FIELD OF VIEW IN CONE-BEAM COMPUTERIZED TOMOGRAPHY ACQUISITION

(71) Applicants: Gloria Menegaz, Verona (IT); Roberto Morsiani, Imola (IT); Bruno Rivalta, Bagnacavallo (IT); Carlo Sandri, Valdagno (IT); Flavio Simonetti, Verona (IT)

(72) Inventors: Gloria Menegaz, Verona (IT); Roberto Morsiani, Imola (IT); Bruno Rivalta, Bagnacavallo (IT); Carlo Sandri, Valdagno (IT); Flavio Simonetti, Verona (IT)

(73) Assignee: CEFLA SOCIETÁ COOPERATIVA, Imola (BO) (IT)

( * ) Notice: Subject to any disclaimer, the term of this patent is extended or adjusted under 35 U.S.C. 154(b) by 272 days.

(21) Appl. No.: 14/517,550

(22) Filed: Oct. 17, 2014

(65) Prior Publication Data

US 2015/0117592 A1 Apr. 30, 2015

(30) Foreign Application Priority Data

Oct. 31, 2013 (IT) .............................. BO2013A0599

(51) Int. Cl.
*A61B 6/00* (2006.01)
*A61B 6/03* (2006.01)
(Continued)

(52) U.S. Cl.
CPC ............ *A61B 6/5264* (2013.01); *A61B 6/032* (2013.01); *A61B 6/4085* (2013.01);
(Continued)

(58) Field of Classification Search
CPC .. A61B 6/032; A61B 6/03; A61B 6/14; A61B 6/4085; A61B 6/5205;
(Continued)

(56) References Cited

U.S. PATENT DOCUMENTS 8,363,780 B2  1/2013 Loustauneau
2008/0187097 A1* 8/2008 Cheng .................... A61N 5/107
                                                    378/65
(Continued)

FOREIGN PATENT DOCUMENTS

EP      1577837       9/2005
WO      2012139031    10/2012

OTHER PUBLICATIONS

Fumihiko Ino et al: "Out-of-core cone beam reconstruction using multiple GPUs", Biomedical imaging: from nano to macro, 2010 IEEE International Symposium, IEEE, Piscataway, NJ, Apr. 14, 2010 Abstract; Fig. 1; Section 3. Methods.

*Primary Examiner* — Dani Fox
(74) *Attorney, Agent, or Firm* — Themis Law (57) ABSTRACT

A method and apparatus for Cone-Beam Computerized Tomography, (CBCT) is configured to increase the maximum Field-Of-View (FOV) through a composite scanning protocol and includes acquisition and reconstruction of multiple volumes related to partially overlapping different anatomic areas, and the subsequent stitching of those volumes, thereby obtaining, as a final result, a single final volume having dimensions larger than those otherwise provided by the geometry of the acquisition system.

20 Claims, 7 Drawing Sheets

(51) Int. Cl.
*G06T 3/40* (2006.01)
*G06T 11/00* (2006.01)
*A61B 6/14* (2006.01)

(52) U.S. Cl.
CPC .......... *A61B 6/5211* (2013.01); *A61B 6/5241* (2013.01); *G06T 3/4038* (2013.01); *G06T 11/008* (2013.01); *A61B 6/14* (2013.01); *A61B 6/5205* (2013.01); *A61B 6/54* (2013.01); *G06T 2200/04* (2013.01); *G06T 2200/32* (2013.01)

(58) Field of Classification Search
CPC . A61B 6/5211; A61B 6/5241; G06T 11/0008; G06T 2200/32; G06T 3/4038
See application file for complete search history.

(56) References Cited

U.S. PATENT DOCUMENTS

| | | | | |
|---|---|---|---|---|
| 2013/0010920 A1* | 1/2013 | Wein | .................. | G06T 11/008 378/19 |
| 2014/0267267 A1* | 9/2014 | Piper | .................. | G09G 5/377 345/424 |

* cited by examiner

METHOD AND APPARATUS FOR INCREASING FIELD OF VIEW IN CONE-BEAM COMPUTERIZED TOMOGRAPHY ACQUISITION

FIELD OF THE INVENTION

The present invention relates to a method and an apparatus for Cone-Beam Computerized Tomography (CBCT) that increases the maximum Field-Of-View (FOV) through a composite scanning protocol, based on the acquisition and reconstruction of multiple volumes by partially overlapping different anatomic areas, and subsequently stitching said volumes, thereby obtaining, as a final result, a single final volume having dimensions larger than those otherwise allowed by the geometry of the acquisition system.

BACKGROUND OF THE INVENTION

CBCT apparatuses are known in the art and provide tomographic images of an anatomic portion by acquiring a sequence of bi-dimensional radiographic images during the rotation of a system that comprises an X-ray source and an X-ray detector around the anatomic part to be imaged.

A CBCT apparatus includes substantially: an X-ray source projecting a conic X-ray beam (unless it is subsequently collimated) through an object to be acquired; a bi-dimensional X-ray detector positioned so as to measure the intensity of radiation after passing through the object; a mechanical support on which said X-ray source and detector are fixed; a mechanical system allowing the rotation and the translation of said support around the object, so as to acquire radiographic images from different positions; an electronic system adapted to regulate and synchronize the functioning of the various components of the apparatus; and a computer or similar, adapted to allow the operator to control the functions of the apparatus, and to reconstruct and visualize the acquired images. There are substantially two kinds of such apparatuses on the market: a first kind where the patient stands or sits vertically during the acquisition, described e.g. in patent EP2018121B1 to Sirona; and a second kind where the patient lies on a table, described e.g. in patent IT1277796 to QR.

In a given CBCT apparatus, the maximum dimension of the volume to be reconstructed, or maximum FOV, is essentially determined by the geometry of the system, in terms of: dimensions of the sensitive area of the detector hit by X-ray, the distances between X-ray source and detector and the rotation axis of the system.

With the aim of obtaining CBCT apparatuses acquiring and reconstructing bigger and bigger volumes, the most direct solutions would lead to larger X-ray detectors, X-ray sources having an ampler angle of beam aperture, and/or an increase of the distance between X-ray source and object to be acquired. Generally speaking, each of these solutions involves significant disadvantages: e.g. economic disadvantages, in that the components are more expensive, or otherwise ergonomic disadvantages, linked to the need to increase the overall dimensions of the apparatus.

The technical problem of increasing the dimension of the maximum FOV without modifying the physical components of the system has already been addressed and solved in different ways, e.g.:

by offsetting the X-ray sensor, as described in U.S. Pat. No. 8,363,780 B2 to Carestream Health/Trophy;

by performing composite trajectories, as described in U.S. Pat. No. 8,300,762 B2 to Morita;

in the slightly different field of hospital bi-dimensional radiography, by summing two subsequent acquisitions of different portions of a long bone to obtain the image of the complete bone, as described in U.S. Pat. No. 7,555,100 B2 to Carestream Health, Inc.

The above solutions each have several drawbacks.

In regard to U.S. Pat. No. 8,363,780, as it appears clear from the description and the figures, by carrying out an offset of the sensor active area, problems arise with the intensity distribution of the radiation on the active surface, thus causing compensation actions to be performed, one of which includes the adjustment of the orientation of the generator as described in said document with reference to FIG. 3c. As illustrated, the effect of the compensation does not fully recover the lack of homogeneity of the distribution of the radiation along the active area of the sensor. Furthermore, there is a relation between the offset of the sensor's active area and the best orientation of the anode of the generator, so that this adjustment step has to be carried out each time an offset value is chosen.

Another drawback can be seen in comparing the scanning process of a traditional CBCT configuration with the one using an offset sensor (FIGS. 2 and 3a to 3c of U.S. Pat. No. 8,363,780). In the traditional configuration, a rotation of 180° allows collecting for each part of the imaged region a complete set of 2D images along the arc. Carrying out the same scanning process along a trajectory of 180° using the offset configuration of FIGS. 3a to 3c reduces the number of 2D images acquired from the peripheral regions, therefore, less information is obtained for the volumetric reconstruction in this region as compared with the traditional configuration of FIG. 2.

In regard to the possible extension of the imaged FOV, the solution according to U.S. Pat. No. 8,363,780, although allowing the acquisition of volumetric images from larger FOV, maintains nevertheless a limit to the FOV dimensions, which depends on the dimensions of the active area of the sensor and the possible maximum offset. Thus in cases where the extended FOV obtained by the sensor's offset is still insufficient for covering the entire region of interest, U.S. Pat. No. 8,363,780 does not suggest a solution for further expanding the FOV so that it covers the region of interest.

The publication "Out-of-core cone beam reconstruction using multiple GPUS" simply suggests how to divide the computational burden of reconstructing the volumetric image out of the set of 2D images acquired during the CBCT scan on several graphic processors, in order to parallelize the reconstruction process that is carried out at the same time on a different part of the acquired image data by each one two or more processing units. This is a conventional processing method which is used in conventional CBCT volumetric imaging for reducing the time needed for the reconstruction of a volumetric image. This document discloses nothing about FOV dimensions and enlargements.

WO2012/139031 discloses generating volumetric images of a large FOV by stitching two dimensional projections. In this document the two dimensional images obtained by the sensor ad related to each of different sensor positions are combined in a bigger 2D image. The volume reconstruction is carried out by using the images obtained by stitching. This method is very sensible to artifact introduced by patient motion or other changes in patient positioning. These changes may occur for each of the 2D images so that the volumetric image is affected by a motion artifact for the entire volume.

SUMMARY OF THE INVENTION

Based on the above, an aim of the present invention is to provide a method and an apparatus overcoming the problems in the known art, configured to provide a reconstructed volume that is bigger than that obtainable through normal acquisition protocols, making use of the stitching of different volumes acquired through subsequent partial acquisitions. Moreover, an aim of the present invention is finding alternative techniques to expand the dimensions of the maximum FOV without the need of modifying the physical components of the system.

These aims are achieved by a method and an apparatus having the features as described hereinafter by means of advantageous embodiments and refinements.

In particular, the problem is solved through a CBCT apparatus capable of extending its maximum FOV through composite acquisition protocols, hereinafter called "Extended View" or EV. In the following description, the normal acquisition protocols are defined as "ordinary", that is, non EV protocols.

An EV protocol comprises essentially N (>1) ordinary acquisitions, which will be herein referred to as "subacquisitions," each comprising a relevant number of projections (e.g. 360), interspersed with repositioning steps during which machine movements modify the relative position of the block comprising X-ray source-detector-mechanical support (defined in the following description as "ray group") with respect to the patient, with the aim of acquiring an adjacent anatomic portion with the subsequent subacquisition. In a system of spatial coordinates integral with the patient, the N volumes resulting from the reconstructions of these subacquisitions, which will be herein referred to as "subvolumes," can have equal or different dimensions, and be in different positions such to cover an overall dimension bigger than the maximum FOV of the apparatus obtainable through ordinary (non EV) acquisition protocols. The positions of the N volumes are such that the union of these volumes shows a continuous anatomic area, bigger than the anatomic area obtainable with an ordinary (non EV) protocol.

The movements for repositioning the system between two subsequent subacquisitions are translational and can occur along any spatial vertical or horizontal axis. The movements can involve patient support (e.g. translation of the table on which the patient is lying), ray group, or both. Performing at least two subacquisitions prolongs the acquisition time of the raw data, and therefore the risk of the patient moving during the acquisition. Two different problems can arise due to patient movement:

in a first case, the patient moves during a subacquisition, producing a motion artifact;

in a second case, the patient remains still during each subacquisition, but moves between two subacquisitions, leading to problems in the registration of two images.

With the aim of obtaining the best possible end result, the repositioning movements must be such as to entirely translate the patient through the support supporting him/her, or maintain the patient in a still position. In this way, the patient remains in the comfortable position (in which he/she was initially positioned) for the whole duration of the EV acquisition protocol, reducing the possibility of movements due to both the second case, as the transition from a subacquisition to the following is smooth and does not induce the patient to modify his/her posture, and the possibility of movements due to the first case, as the patient will not be induced to move during a subacquisition due to an uncomfortable position, different from the initial one. Moreover, as subacquisitions are automatically linked together and performed one after the other, the total acquisition time of EV protocol is minimized. Both these factors (stationarity or comfortable movement of patient and minimization of the overall time) contribute to reduce problems due to patient's movements and improve therefore the quality of final result, preventing possible problems in the registration.

In a first embodiment of the present invention (vertical machines having a C-arm), the patient is only partially fixed to the apparatus through the use of a bite and a craniostat, but he/she is standing or sitting on a surface non integral with the apparatus; bite and craniostat are part of a "patient positioning group" which is a part of the apparatus, but can slide vertically through a slide. The intermediate repositioning occurs through a vertical translation movement of the entire ray group with respect to the patient, at the same time of an opposed vertical sliding movement of the slide of the positioning group, so as to keep the patient in a still position. In a second embodiment (horizontal machines with O-shaped gantry), the patient is lying on a table which is translated through motors controlled by the apparatus.

A first advantage of the present invention consists in providing an apparatus that, the cost of components being equal, can provide reconstructed volumes bigger than what is obtainable with the same X-ray detector without EV protocol.

A second advantage consists in the shortening of acquisition time, through the performance of two or more consecutive subacquisitions, minimizing patient's movements. The repositioning of ray group with respect to the patient occurs automatically, keeping the patient still. In this way both motion artifacts and registration volumes are minimized.

A third advantage lies in the fact that with the present invention radio-opaque markers are not necessary, in that registration is performed on the basis of the anatomic elements present in the volumes to be registered.

A fourth advantage consists in that the volumes are directly registered, without need of volume pre-processing.

A fifth advantage consists in the parallelization of the registration algorithm, which allows reducing the computation times.

BRIEF DESCRIPTION OF THE DRAWINGS

Additional advantages and properties of the present invention are disclosed in the following description and drawings.

DETAILED DESCRIPTION OF EMBODIMENTS OF THE INVENTION

Figure 1:
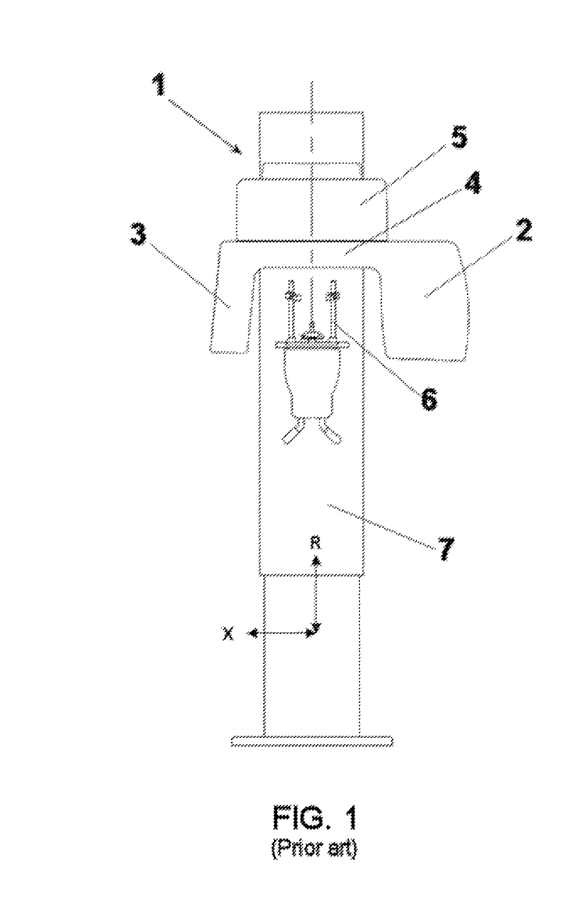
FIG. 1 illustrates an example of a known vertical apparatus.

FIG. 1 shows a vertical apparatus 1 according to the known art, comprising an X-ray source 2 projecting an X-ray cone beam (unless it is successively collimated) through a patient 8, a bi-dimensional X-ray detector 3 positioned to measure the intensity of radiation after it has passed through the object, a C-arm on which said X-ray source 2 and detector 3 are fixed, a mechanical system 5 enabling the rotation and the translation of said support around the patient 8, such to acquire radiographic images from different positions, an electronic system (not shown) capable of controlling and synchronizing the working of the various components of the apparatus, and a computer or similar (not shown) providing control of the apparatus by its user.

As explained above, the block X-ray source-X-ray detector-rotating arm connecting them is collectively called ray group 4. Ray group 4 is provided with three axes of movement: X, Y, and R, i.e. translational movement along the two axes on the horizontal plane, plus rotational movement around the ray group axis. The apparatus comprises also a group 6 for positioning and immobilizing a patient 8, the group 6 in its turn having e.g. a chin holder and temple-holding rods. The apparatus includes also a vertically moving post 7, which is used to adapt the overall height of the apparatus to patient dimensions. The structure of the above-described apparatus is well known in the art.

Figure 2:
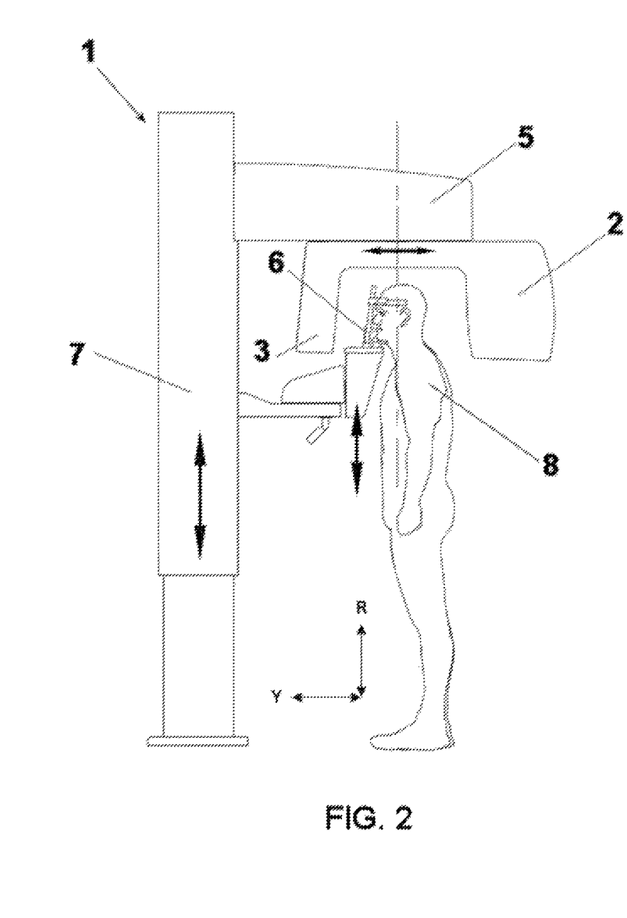
FIG. 2 illustrates a detailed view of a vertical apparatus according to the present invention.

In a first embodiment, the present invention is integrated in the vertical apparatus shown in FIG. 2.

In this first embodiment, patient 8 is positioned in patient positioning group 6, and a first subacquisition of a first subvolume is performed (e.g. of the patient's mandible). At the end of this first subacquisition, either ray group 4 or patient positioning group 6 is re-positioned and a second subacquisition is performed (e.g. of the patient's mandible). Once the two subvolumes have been acquired, they are registered so as to obtain a reconstructed FOV bigger than that obtainable through a single acquisition, as described in the flow chart of FIG. 8.

According to the desired result, a vertical addition (e.g. mandible+maxilla) or a horizontal addition (e.g. right half of arch+left half of arch) may be necessary.

Figure 6:
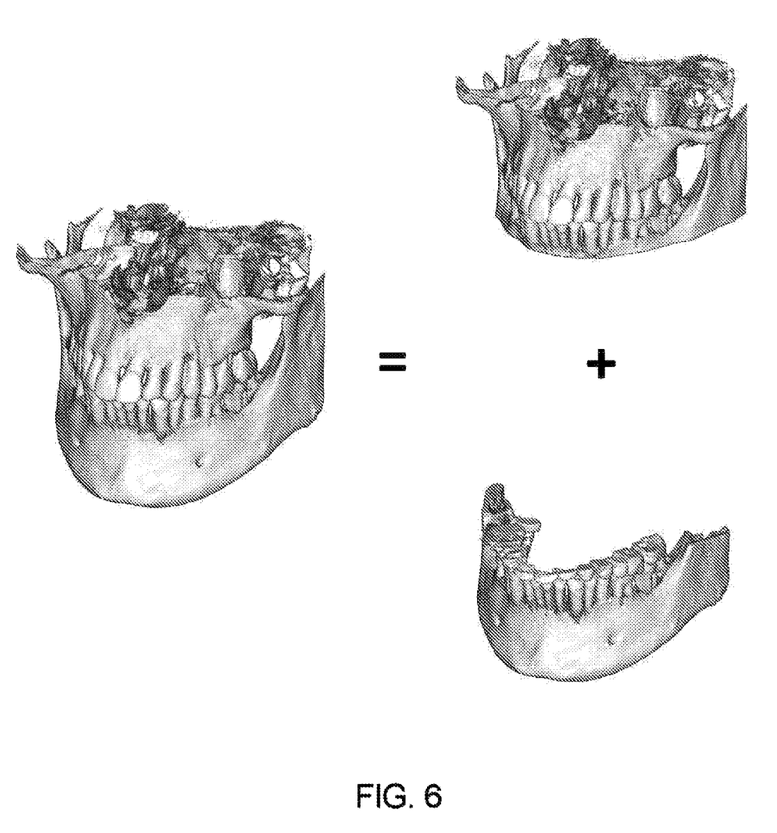
FIG. 6 illustrates an example of an acquisition consisting of two separate vertically translated subacquisitions (maxilla+mandible).

If a vertical volume addition is desired, the repositioning between the subacquisitions occurs with a synchronized movement of the lifting post and of the chin rest in opposed directions so as to leave patient's head still (fixed to the mobile part of chin rest). An example of the result of the vertical volume addition is shown in FIG. 6.

Figure 3:
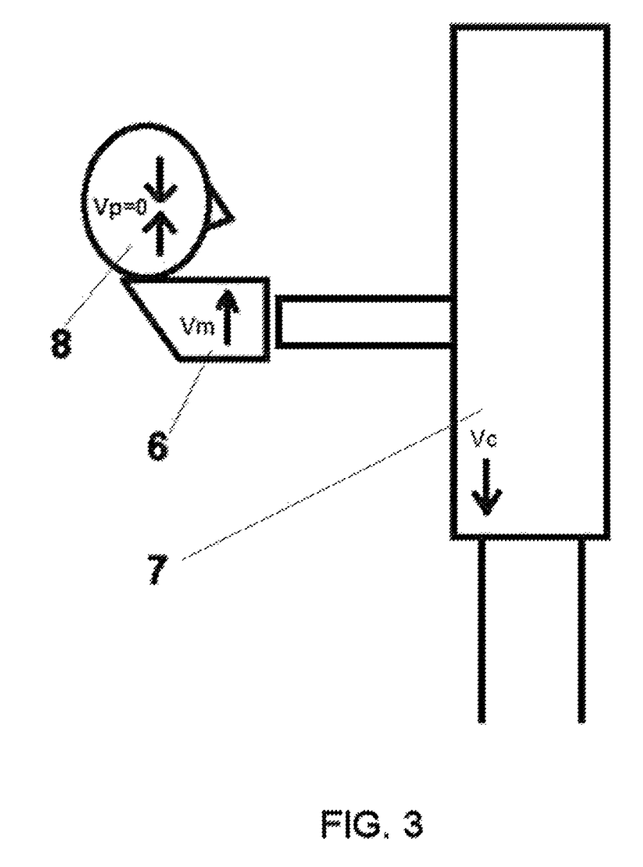
FIG. 3 illustrates a detail of the repositioning movement of a vertical apparatus between two sub acquisitions.

FIG. 3 shows post 7 (moving at speed Vc), chin rest 6 moving, with respect to the post, at speed Vm, and patient 8 remaining still, that is, moving at a speed Vp=Vm−Vc=0.

For the patient to remain still in space (Vp=0) as desired, the movements of the two structures (post and chin rest) must occur in opposite directions, with the same speed in absolute value, the movements being suitably synchronized with each other.

In order to maintain a constant speed, the single movements must be fed back with a speed control. The synchronization between the two movements can be performed directly, by compensating the feedback of each movement with the information of the speed of the other; or indirectly, through an initial lag (of the movements) calibrated to compensate the different reactivity and inertia of the structures, without inter-compensation in real time.

In a preferred embodiment, the first movement (chin holder) is actuated by a stepper motor, intrinsically fed back in position, while the second movement (post) is actuated by an asynchronous motor, electronically fed back in speed (speed can be measured through a hall effect sensor, an encoder, a potentiometer or without sensor). To take into account the inevitable different reactivity and inertia of the two structures, their movements are not started at the same time, but preferably differed with a calibrated lag.

Figure 7:
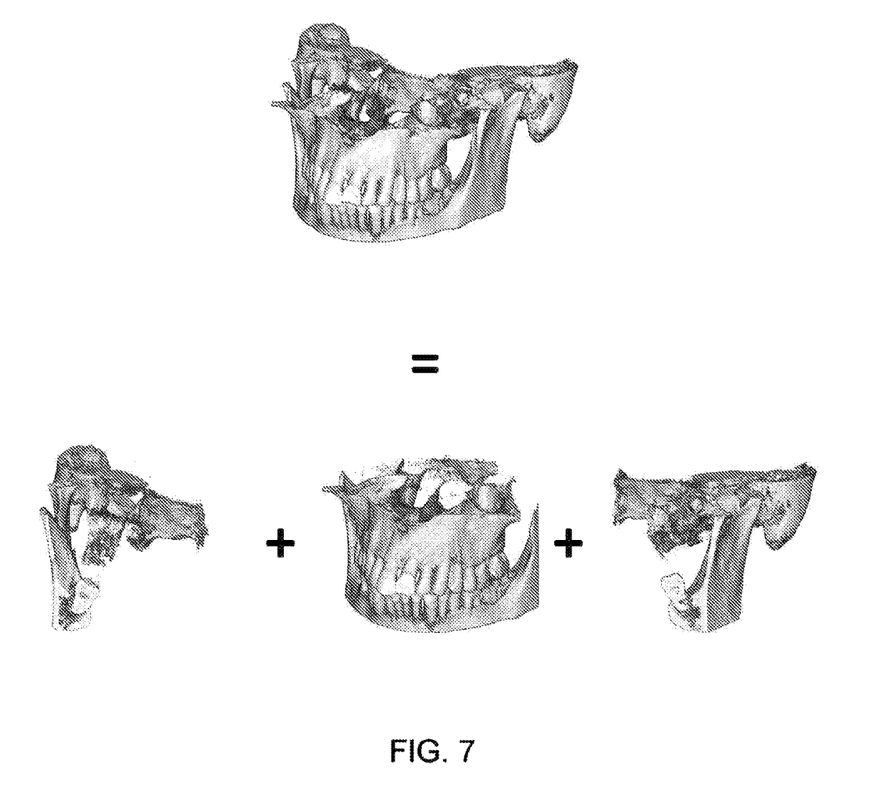
FIG. 7 illustrates an example of an EV acquisition based on three separate horizontally translated subacquisitions (complete dental arch+temporomandibular joints).

If a horizontal volume addition is desired, the possibility of an X-Y movement of ray group 4 is exploited, i.e. substantially the possibility of translating the rotation axis on a perpendicular plane. The step of repositioning occurs through an X-Y translation of ray group 4 with respect to patient, who remains still, so as to better focus the areas of anatomic interest. An example of the result of such horizontal volume addition is shown in FIG. 7.

Figure 4:
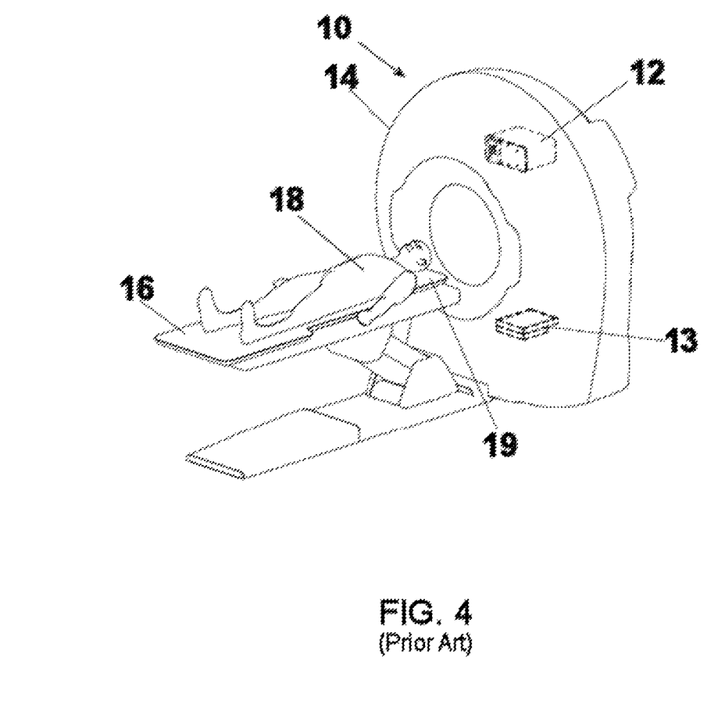
FIG. 4 illustrates an example of a known horizontal apparatus.

FIG. 4 shows instead a typical horizontal apparatus according to the known art, also comprising an X-ray source 12 projecting an X-ray cone beam (unless it is successively collimated) through a patient 18, a bi-dimensional X-ray detector 13 positioned to measure the intensity of radiation after it has passed through the object, a cylindrical gantry (O-shaped gantry) on which said X-ray source 12 and detector 13 are fixed, a mechanical system capable of enabling the rotation of said gantry around the object so as to acquire radiographic images from different positions, an electronic system (not shown) capable of controlling and synchronizing the operation of the various components of the apparatus, and a computer or similar (not shown), capable of providing control of the apparatus by its user. In this embodiment the patient 18 is lying on table 16 and his/her head is kept still through a head-holder helmet (not shown) supported by the terminal portion 19 of the table. With this kind of apparatus, the acquisition of other anatomic portions (e.g. limbs) can be performed, which are supported and fixed to the terminal portion 19 of table 16.

Figure 5:
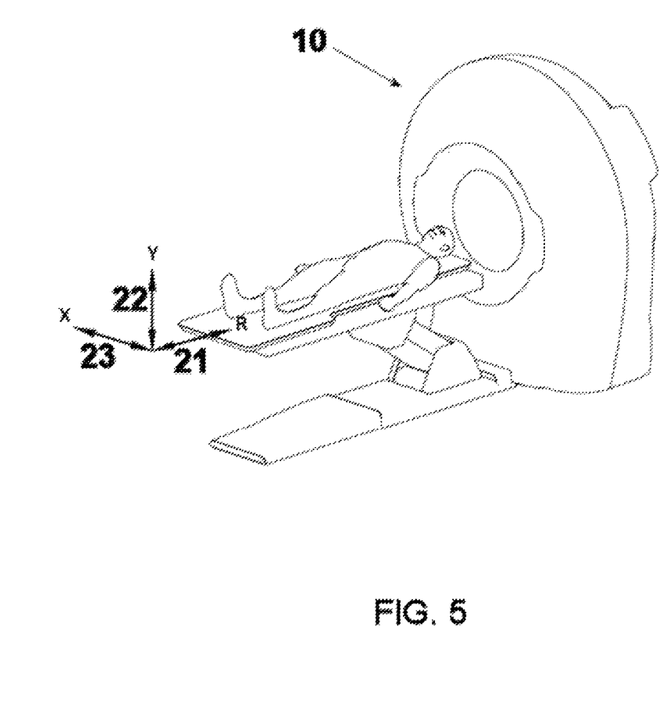
FIG. 5 illustrates a detail of a horizontal apparatus according to the present invention.

A second embodiment relates to the horizontal apparatus shown in FIG. 5.

If a vertical volume addition must be performed, (longitudinal with respect to patient's long axis), the patient is suitably positioned on table 16, and a first subacquisition of a first subvolume is performed (e.g. of the patient's mandible). At the end of this first subacquisition, table 16 is repositioned and a second subacquisition is performed to acquire a second subvolume (e.g. of the patient's maxilla). Once the two subvolumes have been acquired, they are registered so as to obtain a reconstructed FOV bigger than that obtainable through a single acquisition, as described in the flow chart of FIG. 8. In particular, in this case table 16 is translated at a suitable distance along axis 21, perpendicular to the plane of gantry 14. An example of the result of such vertical volume addition is shown in FIG. 6.

If a horizontal volume addition is required (perpendicular to patient's long axis), the possibility of moving table 16 along a right/left axis 23 and up/down axis 22 is exploited, both axis 22 and 23 being parallel to the acquisition plane.

The repositioning step occurs through a translation of table 16 with respect to gantry 14, suitably chosen to best focus the areas of anatomic interest. An example of the result of such horizontal volume addition is shown in FIG. 7.

Figure 8:
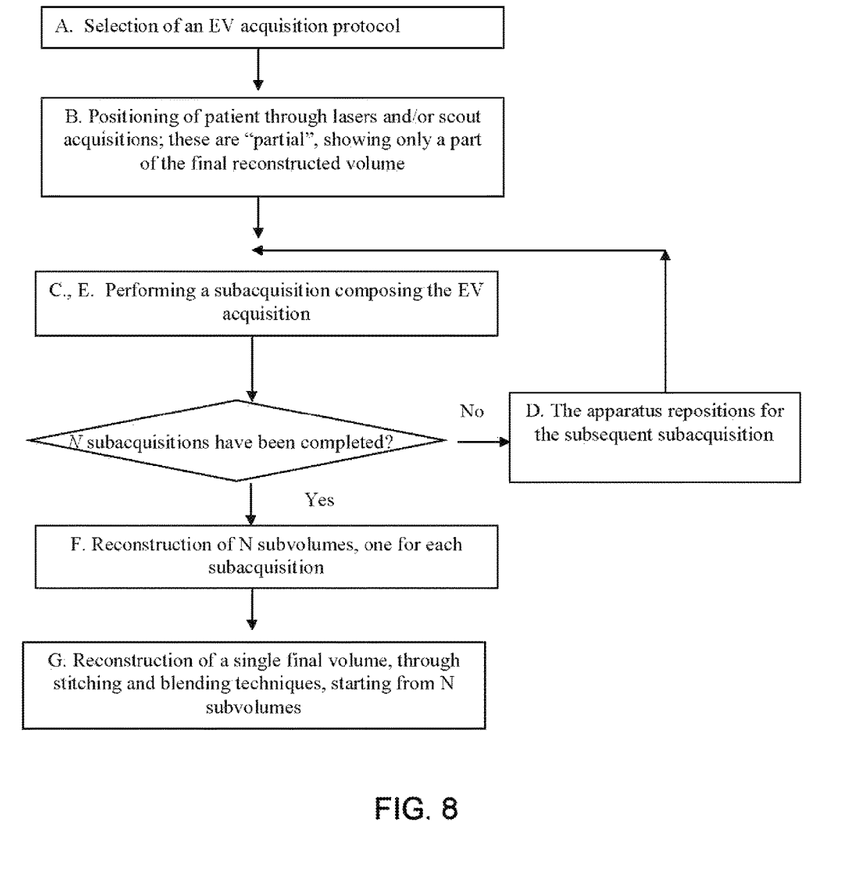
FIG. 8 illustrates a flow chart of a method according to the present invention.

FIG. 8 shows an operational flow chart of a method according the present invention.

The method comprises the following steps:

A. Selection of an EV Acquisition Protocol:

The operator selects the characteristics of the volume to be acquired; on the basis of this choice, the system is configured for a horizontal or vertical volume addition.

B. Patient Positioning:

The operator suitably positions the patient for the acquisition, using the positioning devices. The scout images, which are obtained during the pre-acquisition phase, generally refer to a single subacquisition.

C. Performance of the First Subacquisition:

The acquisition of the raw data is performed for the first anatomic portion to be acquired.

D. The Apparatus is Repositioned for the Following Subacquisition:

The apparatus is automatically repositioned according to the configuration selected in step A.

E. Performance of the Following Subacquisition:

The acquisition of the raw data is performed for the next anatomic portion to be acquired.

F. Then, Steps D and E are Repeated for the Necessary Number of Subacquisitions:

Once the final subacquisition is performed, the acquisition cycle stops.

G. Generation of N Subvolumes, One for each Subacquisition:

The processing of the acquired raw data in each subacquisition generates a subvolume.

H. Reconstruction of a Resulting Single Volume:

The reconstruction of the sum volume occurs through stitching and blending techniques, starting from the N subvolumes.

In order to speed up the procedure, during the N subacquisitions composing an EV acquisition, the rotation direction of the system can be varied: e.g. if during the first subacquisition the rotation direction of the system is clockwise, during the second subacquisition the direction, with respect to the same reference, will be counter-clockwise, so that the starting position of the second subacquisition is nearer to the final position of the first subacquisition, and the EV acquisition procedure is overall shorter, the result being equal.

At the end of the acquisition procedure, the N subvolumes obtained from each subacquisition must be summed so as to form a single overall volume as result of the EV acquisition. This operation cannot be performed as a banal juxtaposition of images for many reasons, especially for the voluntary or involuntary movement of the patient between the sub acquisitions, which would lead to anatomic misalignment in the final volume.

In order to clearly point out the difference between the method according to the present invention and the known techniques, it has to be noted that each sub acquisition related to each different anatomic region in which the global target region is divided is a conventional CBCT acquisition which at the end produces raw image data from which a volumetric image relating to a sub volume covering the corresponding anatomic region is obtained.

The operation of registration of three-dimensional images occurs through the use of known techniques of stitching and blending. In particular, the subvolumes are acquired so as to be partially overlapped, so as to perform the registration in the overlapping region. A typical value of the dimension of the overlapping region is in the range 5-40% of the dimension of a subvolume. The techniques used in this invention are not based on the individuation of "feature point" in the images, but are based on a Mutual information metrics based on a comparison of the information dependency between the entropy of the images, which in a numerical optimization process searches for the geometrical transformation minimizing the overlapping mistake. The process of optimization starts from an initial condition linked to the spatial geometry of acquisition and performs iterations to improve the overlapping of the two subvolumes, maximizing the matching of the images from the informative point of view.

One way of improving the quality of the final reconstruction consists in registering in the sub region excluding the peripheral areas of the volume where the image is noise is more present ("crop").

One way to improve the quality of the blending in the overlapping region consists in combining the grey levels of the starting subvolumes according to weights depending on the pixel position. In the overlapping region of the reconstructed image the pixel assume a value based on the weighted average of the starting subvolumes. The weights are calculated based on the position of each pixel in the overlapping region, in relation to the position of the two involved subvolumes. In other words, the more a pixel is in a peripheral region of a subvolume, the smaller its weight will be.

For a deeper detail: two images are given as input, called fixed and moved, respectively. The fixed image remains fixed in the space, while moved is transformed with a previously transformation calculated through a registration.

The new blended image keeps the original colors of the input images in the non-overlapping areas, while in the overlapping area the color of a pixel results from the weighted sum of the pixels p1 and p2 of the starting images I1 and I2, respectively. The weights are calculated based on the spatial position of p1 and p2 with respect to the overlapping region on a predefined gradient direction: z in the vertical case and x-y in the horizontal case. Therefore, on the extremes of the resulting images, the color of p1 will be prevailing on the color of p2 or vice versa, according to the prevailing position, while in the centre of the overlapping area the resulting color is an average between p1 and p2.

In the particular case of the vertical stitching:

1. the bounding box B of the overlapping area is found, described by the vertexes delimiting the region;

2. height h of B is calculated, as difference between z min and max of the vertexes of B;

3. for each pixel P in the overlapping area and belonging to the fixed image:

a. its geometric position is found P(x,y,z)

b. the distance hr between P and the vertex of B with minimum z, measuring the height of P with respect to the overlapping area, is found c. w=hr/h is found, indicating the weight of the color with respect to its spatial position.

d. being cF e cM the colors of the pixel corresponding to P(x,y,z) respectively for the fixed and moved images, the color c of the pixel is calculated in the blended image through the formula c=w*cF+(1−w)*cM.

By vertical stitching it is intended that the volumetric image of an object having a certain vertical dimension, is obtained by stitching together according to a method according to the present invention at least two images each one relating to one of two parts of the said object which are offset one from the other and adjacent in a vertical direction so to cover the entire object.

According to an additional aspect of the present invention, steps are provided for smoothing or eliminating boundary offsets of each sub volume relatively to the adjacent ones. This is particularly relevant for the so called vertical stitching. This offsets determine that the boundaries of the stitched sub volumes forms small steps and this offsets are due to slight misalignments of the sub volumes according either to slight patient motion between each of the sub acquisitions or of slight displacements within the tolerances of the operative units of the imaging apparatus.

A simple and preferred solution consists in cutting away a peripheral slice of the volume along the boundaries.

Figure 9:
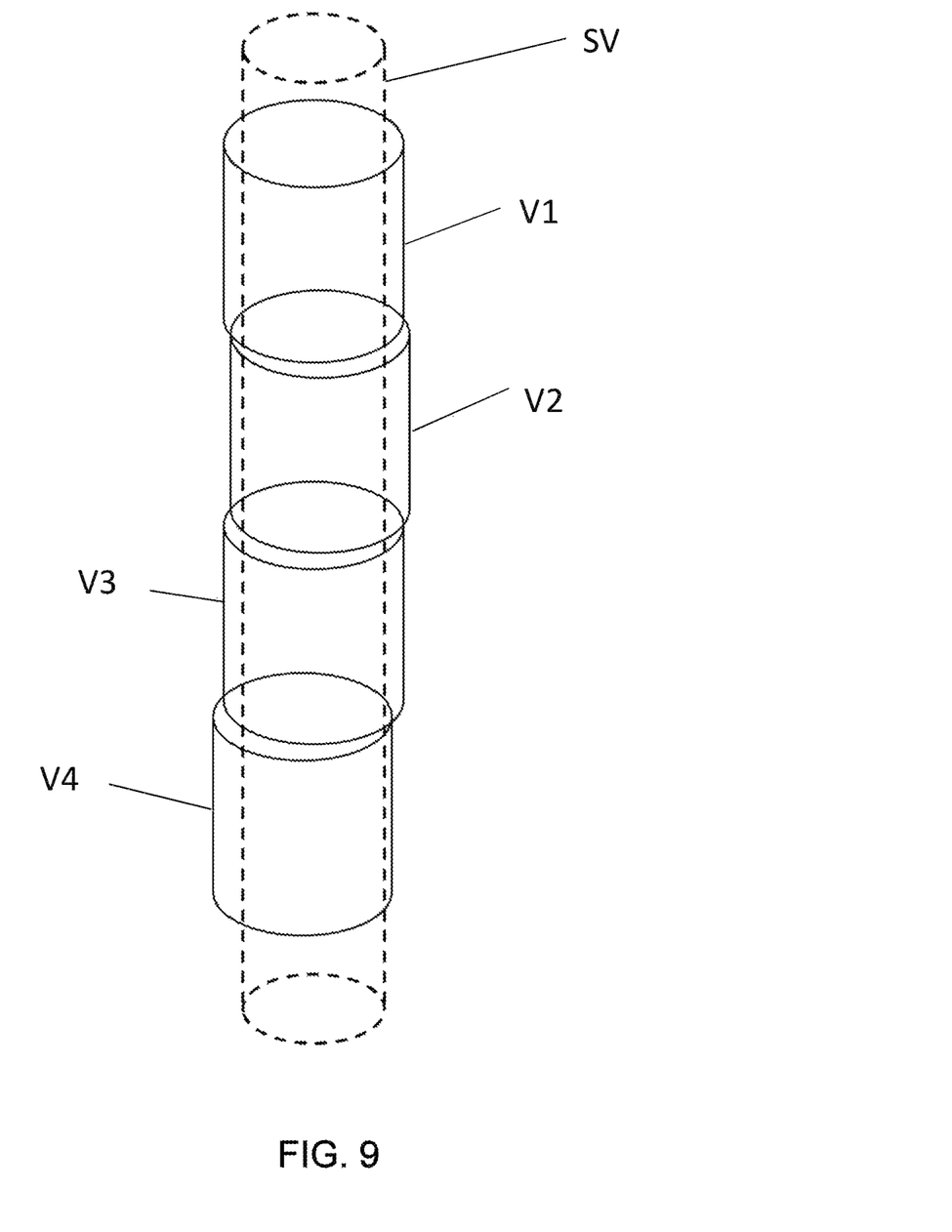
FIG. 9 illustrates diagrammatically the result of the stitching of partial volumes, which relate to vertically aligned partial regions, and the step used to avoid misalignment of the peripheral boundary of the volumetric images related to such partial regions.

FIG. 9 illustrates diagrammatically these steps. In this case, the volumetric image of the region is obtained by sub acquisitions of four sub volumes which are vertically offset and are indicated by V1, V2, V3, V4, The peeling off of a peripheral layer determines that sum volumetric image has a cylindrical boundary as the one indicated by the dotted cylinder SV. The peeled off peripheral layer or slice is the one define by the subtraction of the volume of the sum volumetric image SV and the stitched sub volumes V1, V2, V3 and V4.

Another improvement provided by the present invention relates to not performing the process when the sub volumes or at least the overlapping regions of adjacent sub volumes have a grey level distribution which is highly homogeneous. This is the case when the imaged region comprises soft tissues, fat or the like only.

In this case the images are poor of structural details and registration and stitching may fail to be properly carried out due to the fact that no recognizable pattern is present in the images or at least in the overlapping regions.

Several ways of operating may be chosen.

According to a first way of proceeding when carrying out the stitching algorithm the relative displacements of the adjacent images to be registered and stitched are compared to maximum thresholds values and if these threshold values are overcome a warning is displaced informing the user that the result might be not correct. The warning can be only a message displayed on a screen or it can be accompanied also by acoustic signals or other signaling means.

In another mode of operation according to the invention, the warning may be based on the choice of the anatomic district and the probability that the district includes tissues that might lead to a situation of high homogeneity at least in the overlapping regions where the two adjacent images are matched.

In a preferred embodiment, the generation of the warning signals and/or other actions like stopping the scanning process are carried out according to the result of an automatic quality analysis of the grey level distribution in the image corresponding to the acquired sub volume or sub volumes.

This analysis is performed preferably before stepping forward with the acquisition of the image data for a following sub volume, so to avoid unnecessary exposure of the patient to radiation if the result of the registration process is not reliable.

Several different criteria may be used combined or alternatively to each other for determining quality values of an image.

Since image pixels or voxels are identified by a value representing the grey level and by their position in a two-dimensional or three-dimensional matrix, it is possible to use various algorithms to calculate a value, which is representative of the grey level distribution within the image or a part of it.

Empirically determined values of the quality of the distribution of the grey levels may be compared with the quality of the acquired sub volumes in order to determine whether the grey level distribution in the acquired image is within the range allowing a correct implementation of the stitching process.

For example, a simple mean value of the grey levels, a geometrical mean value, or even more complicated functions such as eigenvalues of the pixel or voxel matrix, gradients and other parameters which are a measure of the feature of the matrix may be used.

Similarly, one or more expert algorithms may be used such as a classification algorithm, a predictive algorithm or a similar algorithm for determining the quality of the image in relation of the distribution of the grey levels.

Another alternative way to automatically evaluate the quality of the distribution of the grey level in an image includes experimentally generating histograms of samples of grey level distributions in the images of target regions or objects corresponding to various conditions and/or tissues and/or anatomic regions, and generating a look up table for the sample grey level distributions. The evaluation of whether an acquired image has the quality required for being correctly processed by the stitching algorithm is made by simply comparing the histograms of the grey level distributions of the images acquired with the histograms representing the sample grey level distribution and determining which of the sample grey level distributions is the nearest to that of the acquired image. Thus, if the nearest sample grey level distribution is one for which the process is not reliable, warning signals are emitted and/or any other action, like stopping the scanning process is performed.

Generally speaking the above improvement of the method consist in:

Defining the possible kind of relative displacements which two images of adjacent sub volumes can be subjected when being processed by the stitching algorithm;

Determining the range of the magnitude of each of the said possible kind of relative displacements for which the stitching algorithm is considered to have been correctly executed;

Generating a table of the said kind of displacements and of the corresponding range of possible magnitudes for which the stitching algorithm is considered to have been correctly executed;

Determining the kind of the relative displacements of the acquired images of adjacent sub volumes and measuring the magnitude of the said relative displacements;

Determining whether the said measured magnitudes for each kind of displacement is within the corresponding range;

Generating a warning signal when the measured magnitude of at least one kind of displacement has a value which is outside the corresponding range of magnitudes.

Such method steps can be carried out by a software, which is executed by the same computer executing the stitching process;

Optionally suggesting or stopping the scanning process in relation of the acquisition of the images for the following sub volumes.

According to the variant in which the criteria for determining if the stitching can be correctly carried out is the level of non-homogeneity of the grey level distribution in the images, the method comprises the following steps:

Experimentally determining the admissible grey level distributions in the images for allowing the stitching process to be carried out correctly;

Setting a tolerance for assessing similarity of two grey level distribution

Measuring the grey level distribution of the image of at least one first sub volume or at least of the overlapping part of this first sub volume with the following one;

Comparing the measured grey level distribution with the experimentally determined one;

Generating a warning signal if the difference of the measured grey level distribution from the most similar admissible grey level distribution is greater than the tolerance for assessing similarity of two grey level distributions;

Optionally suggesting or stopping the scanning process in relation of the acquisition of the images for the following sub volumes.

The tolerance for assessing similarity of two grey level distributions may be computed according to many different algorithm examples of which could be the standard deviation or the minimum square function or other metrics.

Instead of using metrics for determining the level of similarity of two histograms, it is also possible to use classification or predictive algorithm.

A way of numerically representing grey level distributions is a histogram in which the total number of pixels having a grey level falling within a certain range of grey levels is represented.

According to the further variant disclosed above the method comprises the following steps:

Determining a unique numerical quality value of an image as a function of the grey levels of each pixel or voxel of the said image;

Determining experimentally a range of admissible quality values for an image for which the stitching algorithm works correctly;

Calculating the numerical quality value for the image of a first sub volume;

Comparing the said calculate quality value with the experimentally determined range of admissible values for the numerical quality value;

Generating a warning signal when the quality value calculated for the image for the acquired first sub volume falls outside the said experimentally determined range of admissible quality values;

Optionally suggesting or stopping the scanning process in relation of the acquisition of the images for the following sub volumes.

As already disclosed above, many different kinds of functions can be used for calculating a quality value.

A quality value can be computed also by using the data of the histograms representing the grey level distribution over the pixels or voxels of the image. In this case the function could be a simple mean function or other nonlinear mean functions.

Also regarding to the above alternative methods the means for carrying out the method may be in the form of a software carried out by a computer and preferably by the same computer, which executes the stitching and blending software and optionally, also the control of the imaging apparatus.

As an alternative, the hardware/software configuration can be substituted by hardware architecture configured to carry out the method steps.

It is important to notice that a combination of the said different methods can be used. Furthermore when considering the choice of the quality criteria and the functions used for their evaluation several different criteria may be combines as well as several different evaluation functions can be also combined and the results of this evaluations is summarized in a final value according for example a weighted sum of the numerical results of each different evaluation function or method.

Similarly, when considering the method for validating the registration process by determining the magnitudes of the different kind of possible relative displacements of the images of adjacent subvolumes, the results of the comparison of the measured magnitudes of each kind of displacement with the corresponding range or threshold value can be combined into a final global value, which can also be obtained by weighted combination of the results for each kind of displacement. Furthermore it might be elected that in order to consider faulty or non reliable the result of the registration process, at least two or more than one of the different kinds of displacement should show a non admissible magnitude and these data should be combined also with the absolute value of a parameter calculated according of a certain metrics, so that for the validation process both criteria are taken in consideration, namely, the difference from the range of admissible magnitudes and for how many of the different kinds of displacements a non-admissible value of the magnitude has been measured.

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become apparent to those skilled in the art and the scope of the present invention is limited only by the appended claims.

SUMMARY OF REFERENCE CHARACTERS

1 Vertical CBCT apparatus
2 X-ray source
3 X-ray detector
4 Ray group
5 Mechanical system for moving C-arm
6 Patient positioning group
7 Mobile post
8 Patient
10 Horizontal CBCT apparatus
12 X-ray source
13 X-ray detector
14 Cylindrical gantry
16 Table
18 Patient
19 Table end
21 Long table axis
22 Left-right table axis
23 Up-down table axis
V1, V2, V3, V4 volumetric images relating to subvolumes
SV global volumetric image obtained according the method of the present invention

The invention claimed is:
1. A method of increasing Field Of View (FOV) dimensions in an apparatus for cone-beam computerized tomography (CBCT) acquisition, the method comprising:
A. selecting an image data acquisition protocol comprising a sequence of sub acquisition steps, each sub acquisition step including acquiring raw image data of a subvolume covering one of a first or a second adjacent to and partially overlapping anatomic areas;

B. positioning a patient to be imaged;

C. performing a first subacquisition step of the first anatomic area;

D. repositioning the apparatus for a second subacquisition step of said sequence of sub acquisition steps;

E. performing the second subacquisition step of the second anatomic area, said second anatomic area being adjacent to and partially overlapping said first anatomic area;

F. generating volumetric images of first and second subvolumes respectively covering the first and the second anatomic areas starting from the corresponding raw image data acquired during each of the first and the second subacquisition steps; and G. reconstructing a single global volumetric image from said volumetric images of the first and the second subvolumes, wherein the step of reconstructing said single global volumetric image is performed through an image registration process that includes stitching and blending of at least part of said volumetric images of the first and the second subvolumes.

2. The method according to claim 1, wherein a size of an overlapping region of first and second anatomic areas is 5-40% of a size of the first or the second subvolumes.

3. The method according to claim 1, wherein the step of blending the volumetric images of the first and the second subvolumes reconstructs pixels or voxels of the global volumetric image, and wherein grey levels of the pixels or voxels of the global volumetric image maintain original values of the pixels or voxels in the corresponding subvolume in non-overlapping areas of the first and the second subvolumes.

4. The method according to claim 3, wherein, in the blending step of the volumetric images of said first and second subvolumes for reconstructing the pixels or voxels of the global volumetric image, the grey levels of the pixels or voxels of the global volumetric image are combined together by applying weights to each grey level value of each of said pixel or voxel according to a position of said pixel or voxel in the global volumetric image, and wherein the grey levels of said pixels or voxels of the global volumetric image located in an overlapping region of the first and the second subvolumes are determined by assigning to every single pixel or voxel a value of a grey level determined as a weighted average of the grey levels of the corresponding pixels or voxels in the said overlapping region of the global volumetric images corresponding to the overlapping region of the first and the second subvolumes.

5. The method according to claim 1, further comprising the step of cropping by excluding, during the image registration process, a subregion of a peripheral area of a volume where noise is maximum.

6. The method according to claim 1, further comprising a boundary smoothing step by removing, from the global volumetric image, a peripheral external slice resulting from the steps of stitching and blending steps the volumetric images of the first and the second subvolumes.

7. The method according to claim 1, further comprising a validation step of the image registration process which comprises:

defining kinds of relative displacements of the volumetric images of the first and second subvolumes;

setting a range of admissible magnitudes for each of the kinds of relative displacements;

measuring a magnitude of each the kinds of relative displacements that have taken place in registering the volumetric images of the first and the second subvolumes;

comparing the measured magnitudes of each relative displacement that has taken place in the image registration step with the corresponding range of admissible magnitudes;

generating a warning when at least one of the measured magnitudes falls outside the corresponding range of admissible magnitudes; and optionally stopping the image registration process.

8. The method according to claim 7, wherein the validation step of the image registration process is performed immediately after the first and the second subacquisition steps of each of two subsequent subacquisition steps or immediately after each subacquisition step.

9. A CBCT apparatus configured to perform the method for increasing the field of view according to claim 1, the apparatus comprising:

a ray system (4, 14) comprising an X-ray source (2, 12) and a bi-dimensional X-ray detector (3, 13) rigidly fixed to each other (4, 14) and configured to rotate on a rotation axis (R) around a patient to acquire bi-dimensional radiographic raw images;

a patient positioning system (6, 16);

a mechanism for moving one or both of the ray system (4, 14) or the patient positioning group (6, 16) configured to translate an acquisition plane along the rotation axis (R), or to translate the rotation axis (R) in a plane defined by two Cartesian axes (X and Y), between a first subacquisition step and a subsequent second subacquisition step, in order to acquire different contiguous anatomic regions;

an electronic system regulating and synchronizing a functioning of various components of the apparatus; and a computer or processor enabling an operator to control the CBCT apparatus and visualize results, wherein the CBCT apparatus is configured to be automatically repositioned during step D of the method, by repositioning the ray system (4, 14) or the patient (8, 18) according to number and relative positions of subvolumes corresponding to the anatomic regions that generate a global volumetric image covering an entire target region.

10. The CBCT apparatus according to claim 9, wherein the apparatus is configured to have the patient (8) disposed in a vertical position, either sitting or standing, during image acquisition by providing a vertically adjustable post (7) and a chin rest, and wherein repositioning of the apparatus during step D of the method is such that movements of the post and the chin rest, proceed in opposite directions, at a same speed in absolute value, and that the movements of the post and the chin rest are synchronized.

11. The CBCT apparatus according to claim 10, wherein the movements of the chin rest and the post are actuated by different motors controlled to compensate for different reactivity and inertia by providing an adjustable lag.

12. The CBCT apparatus according to claim 9, wherein the apparatus is configured to have the patient disposed horizontally during image acquisition, and wherein the apparatus is further configured to reposition during step D of the method a by moving patient table (16) according three spatial axes (21, 22, 23).

13. The CBCT apparatus according to claim 9, wherein the apparatus is configured to vary direction of rotation of the ray system (4, 14) clockwise or counter-clockwise, between the first subacquisition step and the second subacquisition step, such that a starting position of the subsequent subacquisition step is nearer to a final position of the first subacquisition step, thereby causing extended view (EV) acquisition procedure to be overall shorter.

14. A method of increasing Field Of View (FOV) dimensions in an apparatus for cone-beam computerized tomography (CBCT) acquisition, the method comprising:
   A. selecting an image data acquisition protocol comprising a sequence of sub acquisition steps, each sub acquisition step including acquiring raw image data of a subvolume covering one of a first or a second adjacent to and partially overlapping anatomic areas;
   B. positioning a patient to be imaged;
   C. performing a first subacquisition step of the first anatomic area;
   D. repositioning the apparatus for a second subacquisition step of said sequence of sub acquisition steps;
   E. performing the second subacquisition step of the second anatomic area, said second anatomic area being adjacent to and partially overlapping said first anatomic area;
   F. generating volumetric images of first and second subvolumes respectively covering the first and the second anatomic areas starting from the corresponding raw image data acquired during each of the first and the second subacquisition steps; and
   G. reconstructing a single global volumetric image from said volumetric images of the first and the second subvolumes,
   wherein the step of reconstructing said single global volumetric image is performed through an image registration process that includes stitching and blending of at least part of said volumetric images of the first and the second subvolumes,
   further comprising a prediction step of the image registration process, said prediction step comprising:
   defining a parametric quality criterion representing a measure for a grey level distribution of pixels or voxels in volumetric image data related to the first and the second subvolumes;
   defining a threshold value or a sample value for the parametric quality criterion corresponding to the grey level distribution in the global volumetric image which is admissible for correctly carrying out the image registration process;
   calculating a value of the parametric quality criterion for the acquired global volumetric image;
   comparing the calculated value of the parametric quality criterion with the threshold value or the sample value;
   generating a warning when the calculated value has a difference from the threshold value or the sample value which is greater than a predetermined magnitude; and optionally stopping the image registration process.

15. The method according to claim 14, wherein:
   the parametric quality criterion includes one or more than one of the following functions: eigenvalue of a matrix representing a grey level of pixels or voxels of the global volumetric image, eigenvalue of a matrix of a gradients of the grey level between surrounding pixels or voxels for each pixel or voxel in the global volumetric image, a function of the grey levels of the pixels or voxels in the global volumetric image according to a mean function or metric; and
   the step of comparing is performed by a classification or predictive algorithms or by a functional evaluation functional of a difference.

16. The method according to claim 14, wherein the prediction step of the image registration process is performed immediately after the first and the second subacquisition steps of each of two subsequent subacquisition steps or immediately after each subacquisition step.

17. The method according to claim 14, wherein a size of an overlapping region of first and second anatomic areas is 5-40% of a size of the first or the second subvolumes.

18. The method according to claim 14, wherein the step of blending the volumetric images of the first and the second subvolumes reconstructs pixels or voxels of the global volumetric image, and wherein grey levels of the pixels or voxels of the global volumetric image maintain original values of the pixels or voxels in the corresponding subvolume in non-overlapping areas of the first and the second subvolumes.

19. The method according to claim 18,
   wherein, in the blending step of the volumetric images of said first and second subvolumes for reconstructing the pixels or voxels of the global volumetric image, the grey levels of the pixels or voxels of the global volumetric image are combined together by applying weights to each grey level value of each of said pixel or voxel according to a position of said pixel or voxel in the global volumetric image, and
   wherein the grey levels of said pixels or voxels of the global volumetric image located in an overlapping region of the first and the second subvolumes are determined by assigning to every single pixel or voxel a value of a grey level determined as a weighted average of the grey levels of the corresponding pixels or voxels in the said overlapping region of the global volumetric images corresponding to the overlapping region of the first and the second subvolumes.

20. The method according to claim 14, further comprising the step of cropping by excluding, during the image registration process, a subregion of a peripheral area of a volume where noise is maximum.

* * * * *